(12) United States Patent
Holzmann

(10) Patent No.: US 10,838,090 B1
(45) Date of Patent: Nov. 17, 2020

(54) ADDITIVELY MANUFACTURED RADIOLOGICAL TEST PATTERNS

(71) Applicant: Gammex, Inc., Middleton, WI (US)

(72) Inventor: Jason Holzmann, Waunakee, WI (US)

(73) Assignee: Gammex, Inc., Middleton, WI (US)

( * ) Notice: Subject to any disclaimer, the term of this patent is extended or adjusted under 35 U.S.C. 154(b) by 0 days.

(21) Appl. No.: 16/100,647

(22) Filed: Aug. 10, 2018

Related U.S. Application Data

(60) Provisional application No. 62/543,592, filed on Aug. 10, 2017.

(51) Int. Cl.
| | | |
|---|---|---|
| *G06T 7/00* | (2017.01) | |
| *G06T 15/08* | (2011.01) | |
| *G06T 11/00* | (2006.01) | |
| *G01T 7/00* | (2006.01) | |
| *B33Y 10/00* | (2015.01) | |
| *B33Y 70/00* | (2020.01) | |
| *B33Y 80/00* | (2015.01) | |
| *A61B 6/00* | (2006.01) | |
| *B29C 64/118* | (2017.01) | |
| *B29L 31/00* | (2006.01) | |
| *B29K 55/02* | (2006.01) | |
| *B29K 509/02* | (2006.01) | |

(52) U.S. Cl.
CPC .............. *G01T 7/005* (2013.01); *A61B 6/583* (2013.01); *B29C 64/118* (2017.08); *B33Y 10/00* (2014.12); *B33Y 70/00* (2014.12); *B33Y 80/00* (2014.12); *B29K 2055/02* (2013.01); *B29K 2509/02* (2013.01); *B29L 2031/753* (2013.01)

(58) Field of Classification Search
CPC ..... G06T 7/0002; G06T 15/08; G06T 11/008; G01T 7/005; B33Y 10/00; B33Y 70/00; B33Y 80/00; B29C 64/118; A61B 6/583; B29K 2055/02; B29K 2509/02; B29L 2031/753
USPC ........................................................ 378/207
See application file for complete search history.

(56) References Cited

U.S. PATENT DOCUMENTS

| | | | |
|---|---|---|---|
| 5,121,329 A | 6/1992 | Crump | |
| 5,164,978 A * | 11/1992 | Goodenough | A61B 6/583 250/252.1 |
| 5,856,415 A | 1/1999 | Lagace et al. | |
| 5,910,975 A * | 6/1999 | Floyd | G09B 23/286 378/207 |
| 5,968,561 A | 10/1999 | Batchelder et al. | |
| 6,280,785 B1 | 8/2001 | Yang et al. | |
| 6,899,777 B2 | 5/2005 | Vaidyanathan et al. | |
| 7,604,470 B2 | 10/2009 | LaBossiere et al. | |

(Continued)

FOREIGN PATENT DOCUMENTS

WO   WO 2018059473   4/2018

*Primary Examiner* — Taeho Jo
(74) *Attorney, Agent, or Firm* — Andrus Intellectual Property Law, LLP

(57) ABSTRACT

A radiological evaluation device and a method of constructing a radiological evaluation device include a first high-Z material. A first test pattern is constructed by extruding a first high-Z material according to a first test pattern design file. The first high-Z material is combined with a second material to construct the first test pattern. The first high-Z material is radiologically distinct from the second material. A phantom body is constructed. The first test pattern is secured to the phantom body.

27 Claims, 4 Drawing Sheets

(56) References Cited

U.S. PATENT DOCUMENTS

| | | | | |
|---|---|---|---|---|
| 8,445,840 | B2* | 5/2013 | Feke | A61B 5/0059 |
| | | | | 250/252.1 |
| 9,526,471 | B2* | 12/2016 | Goodenough | A61B 6/58 |
| 9,669,116 | B2* | 6/2017 | Baiu | A61K 49/0419 |
| 10,026,513 | B2 | 7/2018 | Cardon et al. | |
| 2004/0227069 | A1* | 11/2004 | Sendai | G16H 30/40 |
| | | | | 250/252.1 |
| 2005/0134264 | A1* | 6/2005 | Speckner | G01R 33/58 |
| | | | | 324/307 |
| 2006/0056580 | A1* | 3/2006 | Frangioni | G01N 23/223 |
| | | | | 378/18 |
| 2009/0067582 | A1* | 3/2009 | Feke | A61B 6/587 |
| | | | | 378/207 |
| 2009/0268876 | A1* | 10/2009 | Crucs | G01D 18/00 |
| | | | | 378/207 |
| 2012/0051523 | A1* | 3/2012 | Feke | A61B 5/0035 |
| | | | | 378/205 |
| 2014/0072108 | A1* | 3/2014 | Rohler | A61B 6/582 |
| | | | | 378/207 |
| 2016/0015356 | A1* | 1/2016 | Baiu | A61B 6/583 |
| | | | | 378/207 |
| 2016/0289468 | A1* | 10/2016 | Turner | B22F 1/0059 |
| 2016/0314570 | A1* | 10/2016 | Goodenough | A61B 6/583 |
| 2018/0140272 | A1* | 5/2018 | Ruchala | A61B 6/032 |
| 2018/0158372 | A1* | 6/2018 | Wang | B33Y 80/00 |
| 2018/0161882 | A1 | 6/2018 | Stawovy et al. | |
| 2018/0161883 | A1 | 6/2018 | Sawovy et al. | |
| 2018/0267127 | A1* | 9/2018 | Geiger | B29C 64/112 |
| 2018/0345583 | A1* | 12/2018 | Leng | G09B 23/286 |
| 2019/0110771 | A1* | 4/2019 | Jhao | A61B 6/583 |

* cited by examiner

ADDITIVELY MANUFACTURED RADIOLOGICAL TEST PATTERNS

CROSS-REFERENCE TO RELATED APPLICATION

The present application claims priority of U.S. Provisional Patent Application No. 62/543,592, filed on Aug. 10, 2017, the content of which is hereby incorporated herein by reference in its entirety.

BACKGROUND

Quantifying high contrast resolution of computed tomography systems is part of many hospitals' quality management requirements and is thus performed at regular intervals. The American College of Radiology (ACR) CT image quality phantom Model 464, available from Sun Nuclear Corp., achieves the imaging needs for current quality management requirements. The Model 464 phantom provides pairs of a high-atomic-number (Z) material next to a low-atomic-number material in what is known as a line pair. The number of line pairs per unit distance is the typical parameter used for measuring high contrast resolution. The Model 464 provides several line pair targets at sequential values ranging from obvious detectability (low resolution) to beyond a threshold of current detectability (high resolution). The thickness of the line pair wafers becomes thinner in order to fit a greater number of line pairs per unit length, i.e. centimeters, and at a certain threshold the diagnostic imaging system, e.g. CT machine, is no longer able to resolve individual wafers from one another. Resolution limitations for CT are typically attributed to both hardware (detector specifications) and software (techniques used for image reconstruction).

Line pairs are typically constructed with layers of aluminum (high-Z) and polystyrene (low-Z). These materials are machined to exacting specifications to achieve the wafer dimensions (e.g. thickness) needed to test various resolution levels. While machining the wafers to a precise thickness tolerance presents one challenge, adhering increasingly large numbers of increasingly thinner wafers per unit length (e.g. centimeter) is a further challenge. As the wafers become thinner, the adhesive layer itself becomes a larger percentage of the line pair thickness and must be accommodated in the phantom design and testing procedures.

New high-Z materials are becoming available. Exemplarily, high-Z materials are available that combine a thermoplastic material with a heavy metal source. Thermoplastic materials may include, but are not limited to: acrylonitrile-butadiene-styrene (ABS), acrylonitrile-styrene-acrylate (ASA), polycarbonate (PC), high density polyethylene (HDPE), and polylactic acid (PLA). The heavy metal source may include, but is not limited to: aluminum (Al), titanium (Ti), bismuth (Bi), iron (Fe), copper (Cu), zinc (Zn), silver (Ag), nickel (Ni), iodine (I), barium (Ba), tin (Sn), tantalum (Ta), cesium (Cs), antimony (Sb), gold (Au), lead (Pb), and tungsten (W), as well as oxides, nitrides, or alloys thereof. Further examples of high-Z materials are disclosed in greater detail in US2016/0289468 and US 2015/0348660, which are incorporated herein by reference in their entireties.

BRIEF DISCLOSURE

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a method of constructing a radiological calibration device, the method including: constructing a first test pattern by extruding a first high-Z material according to a first test pattern design file; constructing the first test pattern by combining the first high-Z material with a second material, the first material being radiologically distinct from the second material; constructing a phantom body of a radiologically neutral material; and securing the first test pattern to the phantom body. Other embodiments of this aspect include corresponding computer systems, apparatus, and computer programs recorded on one or more computer storage devices, each configured to perform the actions of the methods.

Implementations may include one or more of the following features. The method where the radiologically neutral material is a water equivalent material. The method where constructing the first test pattern includes simultaneously extruding the first high-Z material and the second material, where the extrusion of the second material is according to the first test pattern design file. The method where constructing the first test pattern includes sequential extruding the first high-Z material, then extruding the second material, where the extrusion of the second material is according to the first test pattern design file. Further exemplary embodiments of the method may include constructing the first test pattern by extruding the second material according to the first test pattern design file, stopping extrusion of the first material, and/or continuing construction of the first test pattern by extruding a third material according to the first test pattern design file, the third material being radiologically distinct from the first material and the second material. The first portion of the first test pattern may include the first high-Z material and the second material and a second portion of the first test pattern may include the second material and the third material. The first test pattern can be constructed simultaneous to construction of a portion of the phantom body. Both the first test pattern and the phantom body can be constructed by 3D printing. A first portion of the first test pattern may be constructed by extrusion of the first high-Z material and the second material may form a second portion of the first test pattern surrounding the first portion.

Exemplary embodiments of the method may further include operating a 3D printer according to a first test pattern design file to extrude the first material and to extrude the second material to construct the first test pattern. An image of a physiological feature of a patient may be acquired and the first test pattern digitally designed from the image to create the first test pattern design file. The he first test pattern may be constructed using 3D printing according to the first test pattern design file. The first test pattern may include alternating layers of the first material and the second material, where the first material is a low-Z material the second material includes the low-Z material in combination with a metal additive such that the second material is a high-Z material. The high-Z material may be zinc oxide. A plurality of test patterns may be constructed, where the plurality of test patterns include the first test pattern. The first test pattern may be constructed by extruding the second material according to the first test pattern design file and constructing the first test pattern by extruding a third material according to the first test pattern design file. The first material, second material, third material may each be different from the other two in at least one of physical density, electron density, CT number, or attenuation. The phantom body may include a plurality of voids within the phantom body, each of the voids in the plurality of voids dimensioned to securely receive the first test pattern therein. The first test pattern can be secured to the base by a friction fit.

In exemplary embodiments, each test pattern of the plurality of test patterns includes alternating layers of the first material and the second material, where the first material is a low-Z material the second material includes the low-Z material in combination with a metal additive such that the second material is a high-Z material, and each test pattern of the plurality of test patterns includes a different thickness of the alternating layers of the first material and the second material. A first material and a second material of a first operative region can be secured by intra-material diffusion between the first material and the second material. The test pattern can include the first material and the second material. The first operative region further includes a third material surrounding the test pattern. The test pattern may include alternating layers of the first material and the second material forming a series of line pairs across the test pattern. In an exemplary embodiment, each layer of the alternating layers is less than 200 microns in thickness. The first material may be a base material and the second material is the base material in combination with a metal additive to create a high-Z material. The base material may have a CT number between −106 and 106 at 120 kvp. The base material may be ABS plastic. The high-Z material may be zinc-oxide. The high z material may have a CT number greater than 300 and less than 3000 HU at 120 kvp. A phantom body may be constructed of a radiologically neutral material and a first operative region of the calibration device is secured within the phantom body. The phantom body of the calibration device may include an aperture and the first operative region. A phantom insert may be configured to be removably secured within the aperture. Implementations of the described techniques may include hardware, a method or process, or computer software on a computer-accessible medium.

One general aspect of the present disclosure includes a method where the second portion of the first test pattern is injection molded about the first portion. Other embodiments of these aspects include corresponding computer systems, apparatus, and computer programs recorded on one or more computer storage devices, each configured to perform the actions of the methods.

Implementations may include one or more of the following features. Each test pattern of the plurality of test patterns may include alternating layers of the first material and the second material. The first material may be a low-Z material the second material includes the low-Z material in combination with a metal additive such that the second material is a high-Z material. Each test pattern of the plurality of test patterns may include a different thickness of the alternating layers of the first material and the second material.

In embodiments of the calibration device the first material and the second material of the first operative region are secured by intra-material diffusion between the first material and the second material. The test pattern may include the first material and the second material. In an embodiment, the first operative region further includes a third material surrounding the test pattern. The test pattern may include alternating layers of the first material and the second material forming a series of line pairs across the test pattern. Each layer of the alternating layers may be less than 200 microns in thickness. The first material may be a base material and the second material may be the base material in combination with a metal additive to create a high-Z material. The base material exemplarily has a CT number between −106 and 106 at 120 kvp. The base material may be ABS plastic. The high-Z material may be zinc-oxide. The high-Z material may have a CT number greater than 300 and less than 3000 HU at 120 kvp. The phantom body may be constructed of a radiologically neutral material, where the first operative region is secured within the phantom body. The phantom body ma include an aperture and the first operative region is a phantom insert configured to be removably secured within the aperture. Implementations of the described techniques may include hardware, a method or process, or computer software on a computer-accessible medium.

One general aspect includes a calibration device including: a first operative region including: a test pattern, the test pattern including at least a first material and the first operative region including at least the first material; and a second material secured to the first material. Other embodiments of this aspect include corresponding computer systems, apparatus, and computer programs recorded on one or more computer storage devices, each configured to perform the actions of the methods.

Implementations may include one or more of the following features. The calibration device may include the first material and the second material of the first operative region are secured by intra-material diffusion between the first material and the second material. The calibration device test pattern may further include the first material and the second material. The calibration device first operative region may further include a third material surrounding the test pattern. The calibration device test pattern may include alternating layers of the first material and the second material forming a series of line pairs across the test pattern. Each layer of the alternating layers may be less than 200 microns in thickness. The first material is a base material and the second material is base material in combination with a metal additive to create a high-Z material. Implementations of the described techniques may include hardware, a method or process, or computer software on a computer-accessible medium.

DETAILED DISCLOSURE

Additive manufacturing with high-Z materials may be used as a method of manufacturing to create test patterns and quality assurance phantoms for diagnostic imaging systems that utilize ionizing radiation, such as x-rays. One type of test pattern may be used in a high contrast resolution phantom capable of testing and calibrating high resolution computed tomography (CT) imaging systems.

In exemplary embodiments as disclosed herein, additive manufacturing techniques may include 3D printing, for example, fused filament fabrication (FFF) or fused deposition modeling (FDM) while in other embodiments, wafers are extruded at higher tolerances then are available using present-day test pattern manufacturing "subtractive" techniques, such as machining or etching. In embodiments of extruded wafers, wafers may be bonded in the currently available manners, yet improved wafer thickness by extrusion may result in a more accurate test pattern in phantoms. In other embodiment, extruded wafers may be bonded in a new and more advantageous manner, including, but not limited to, fusing.

Figure 1:
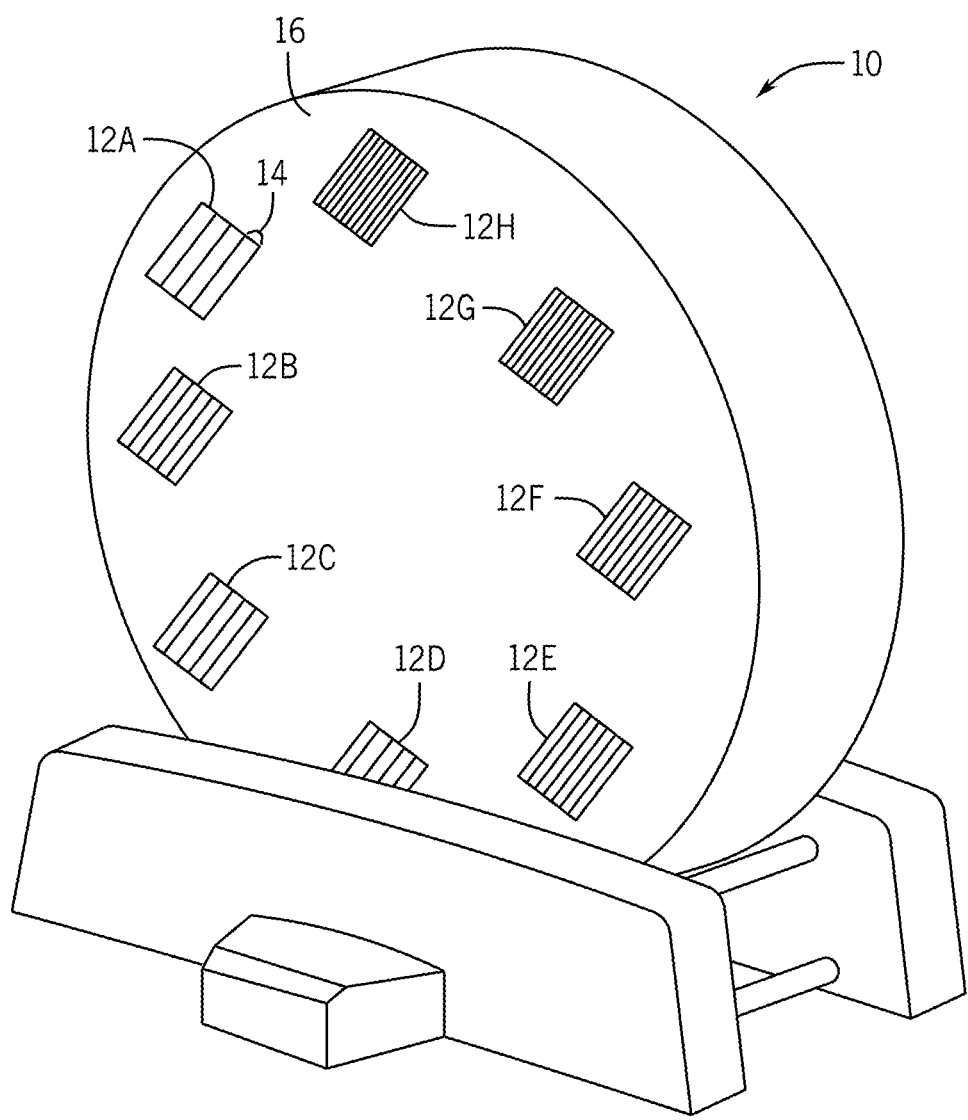
FIG. 1 depicts an exemplary embodiment of a phantom containing high-contrast resolution test patterns.

FIG. 1 depicts an exemplary embodiment of a radiological calibration device in the form of a phantom 10 which is exemplarily a high-contrast resolution phantom and includes a plurality of resolution test patterns 12A-12H. Each resolution test pattern is constructed with a plurality of line pairs 14. Each line pair 14 includes a layer of high-Z material and a layer of a low-Z material. The test patterns 12 each exemplarily comprise a plurality of adjacent line pairs 14. The spatial density of the line pairs within a particular unit of dimension of the test pattern results in a particular resolution pattern capable of testing an imaging system's resolvability.

In the present disclosure, the Z-value represents radiological contrast and therefore represents an absolute scale of CT number or Hounsfield unit of material. The scale is in reference to the radiodensity of water at STP (zero HU). The radiodensity of air at STP is −1000 HU, while the radiodensity of radiopaque elements of materials is frequently 100 HU or greater. Therefore, as used herein, low-Z materials are those close to 0 HU, and for example between +/−100 HU, or +/−106 HU or +/−120 HU. On the other than as used herein, the high-Z material exemplarily provides at least 200 HU of contrast from the low-Z material and is exemplarily greater than 300 HU. In more specific embodiments, the high-Z material, as described herein is between 2000-3070 HU. In still further exemplary embodiments, the high-Z material is below 3070 HU. As will be explained herein, certain reconstruction errors can be minimized or avoided if the x-ray controller is not saturated by the high-Z material.

The body 16 of the phantom 10 is exemplarily constructed of a radiologically neutral material. A radiologically neutral material may be a material that is similar to composition of patient soft tissue in one or more radiological properties. For example, a radiologically neutral material may be a water mimicking material as provided by the SOLID WATER® material available from Sun Nuclear Corp. Non-limiting examples of material for the body of the phantom are further provided in U.S. Pat. No. 9,669,116, entitled, "Water-Equivalent Phantom" and US Patent Application Publication No. 2016/0015356, entitled "Brain Tissue Equivalent Material and Phantom Device comprising the Same," which are incorporated by reference herein in their entireties. In other embodiments, the radiologically neutral material may be one that minimizes interaction or interference with radiation. A radiologically neutral material may be one that exhibits little attenuation or scattering of radiation, or one that includes air, pockets of air, or a material that is radiologically similar to air, as compared to other phantom body materials.

Each of the resolution test patterns 12A-12H are exemplarily formed as an insert into the body 16 of the phantom 10. The inserts may extend through the thickness of the phantom 10 so that resolution at various reconstruction slice thicknesses and field/collimation sizes may be tested with the phantom 10. In construction, inserts may be removable or fixed relative to the body 16 of the phantom 10. As described in further detail herein, improved test pattern inserts can be provided to not only result in a phantom 10 capable of testing higher resolutions than are currently available, but also altogether new test patterns, resulting in new test pattern inserts.

In an exemplary embodiment, an additive manufacturing technique, for example, fused deposition modeling (FDM) may be used to construct the radiological test pattern inserts. In embodiments, a low-Z thermoplastic material is paired with a high-Z infused thermoplastic material. In an exemplary embodiment, bonding between layers is exemplarily addressed by using a low-Z form and a high-Z form of the same thermoplastic material. In an exemplary embodiment, this may be provided by starting with a thermoplastic material having a low-Z value. The high-Z form of the thermoplastic material may be provided by doping the thermoplastic material with a high-Z material, exemplarily a metal or metal compound. A natural affinity due to common atomic structure, functional groups, and physical properties exists in both the low-Z material and the high-Z material because of the common base thermoplastic material. In such an embodiment, adjacent layers of the high-Z material and low-Z material of the test pattern exhibit inherent bonding and adherence when extruded at temperatures above their melting point.

The present application includes disclosure of multiple embodiments of methods of construction of test patterns and radiological calibration devices that include test patterns. In some embodiment, entire layers or wafers of the high-Z or the low-Z thermoplastic material are extruded relative to an adjacent layer or layers. In an embodiment, this may result in an extruded test pattern that includes multiple extruded layers forming line pairs. The extruded test pattern may then be cut to size for use in connection with radiological calibration devices. In other embodiment, the sequential layers of high-Z or low-Z material may be extruded, for example, in an FFF or FDM process using a print head smaller than the test pattern layer area. The control and extrusion characteristics of the print head and the thermoplastic material can be controller to achieve a repeatable incremental layer at the desired line pair spacing. For larger line pair spacing, multiple passes of the print head are used to provide the desired line pair spacing. In one exemplary embodiment, differing line pair spacings are controlled with carrying number passes of the print head with a single material, while in other embodiments, the line pair spacing is controlled by the volume and speed of the extrusion through the print head to provide each layer in the line pair in a single pass of the print head.

In a first merely exemplary embodiment, the thermoplastic material is ABS. The ABS on its own exhibits a low-Z. Additionally, ABS may be doped with titanium (Ti) as the additive to create a high-Z ABS material. Using these materials as an example, the bonding between the layers/materials is related to the functional groups of the materials. ABS has three functional groups while basic polystyrene (PS) has only one functional group. These functional groups create strong bonds between like parts. Since the ABS+Ti material is mostly ABS, the chemistry between the ABS layer and the ABS+Ti layer is similar enough to maintain the strength of a bond between layers of ABS. Additionally, further advantage is gained if the two materials have similar glass transition temperatures. If the glass transition temperatures are similar, then it is likely that both materials can be extruded through a 3D printer without changing nozzle temperature and quickly form bonds with neighboring molecules.

In a second merely exemplary embodiment, the thermoplastic is PLA. The PLA exhibits a low-Z and is used to provide the low-Z wafers and the PLA material is exemplarily doped with stainless steel particles to provide the high-Z version of the PLA material. In embodiments, the high-Z materials may be doped to a radiographic density similar to that of aluminum to maintain consistency with previous tests of calibrations. In other embodiments, two or more doped versions of the base thermoplastic material may be used to provide test pattern inserts with a plurality of effective Z values.

Figure 2:
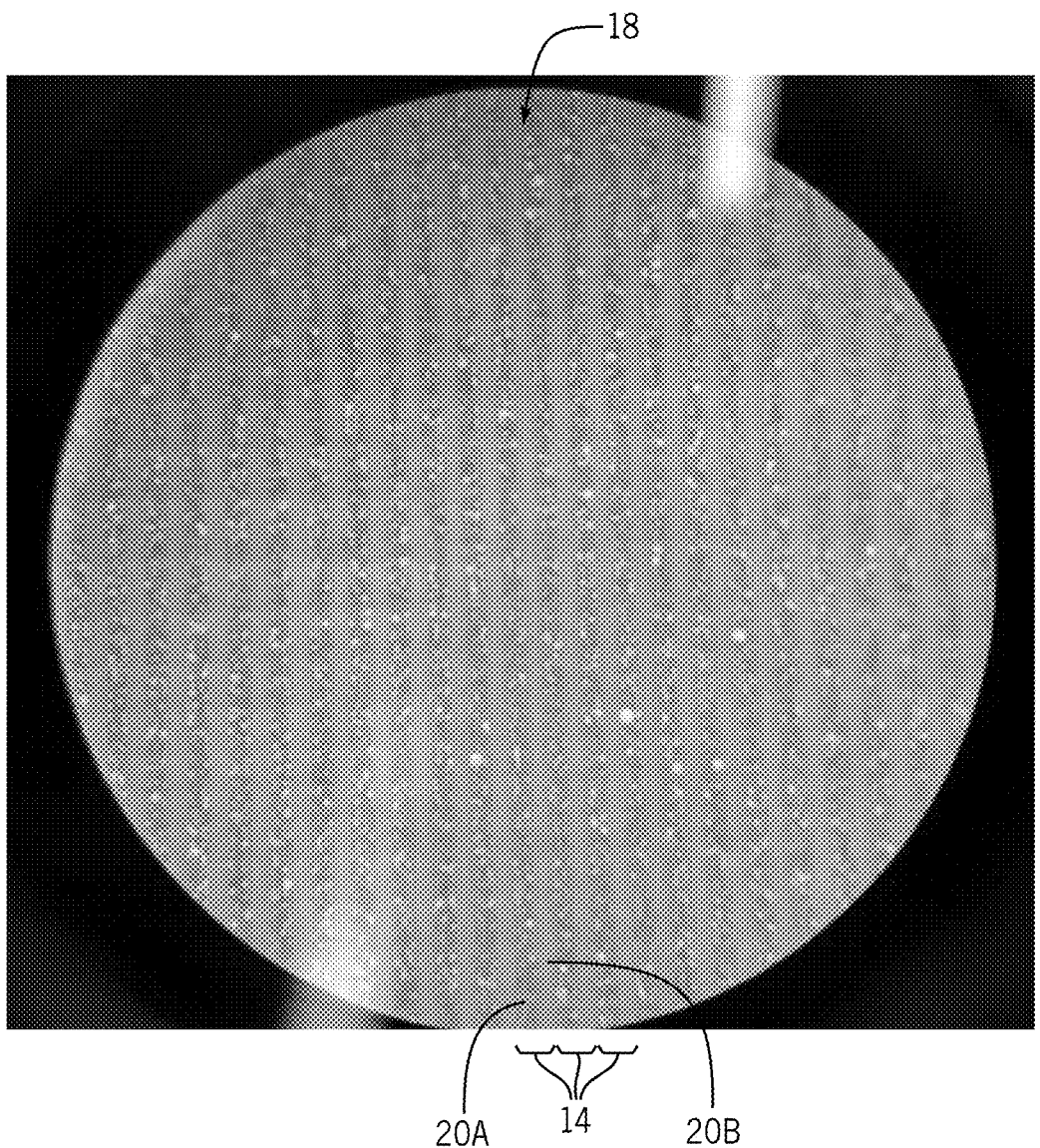
FIG. 2 is a magnified photograph of an exemplary embodiment of a high-contrast resolution test pattern.

The thermoplastic portions of either of the exemplary compositions are the same and adjacent high-Z and low-Z wafers in a test pattern insert will have an affinity to bond to one another. For example, extruding the high-Z and low-Z wafers exemplarily described above in a sequential manner result in a strong bond between the adjacent layers without an external adhesive. Instead the extrusion of the subsequent layer is melted while being extruded onto the previous layer, and since both layers include the same thermoplastic material, the adjacent high-Z and low-Z wafers produce a strong bond. By extruding the wafers as thin layers, the thickness of each wafer can be controlled more closely, resulting in a more accurate wafer thickness versus prior manufacturing processes and products. FIG. 2 is a close up photograph of an exemplary embodiment of a test pattern 18 created in the manners as disclosed herein having a plurality of line pairs 14 comprised of wafers 20A, 20B approximately 200 microns in width.

In exemplary embodiments, adjacent layers of high-Z and low-Z material may be simultaneously extruded such that both layers contact while above their glass transition temperatures which facilitates fusion between the layers, securing the layers without adhesive. In further embodiments, one material of the test patterns is extruded at a time, for example a full layer extrusion or in a deposited layer across the area of the test pattern. Sequential extrusion of a subsequent layer of a second radiologically distinct material with the same thermoplastic base is performed while the previous layer is till above ambient and the new layer introduces additional heat to the system which raises the temperature of the previous layer further facilitating fusion between adjacent layers of the test pattern.

Figure 3:
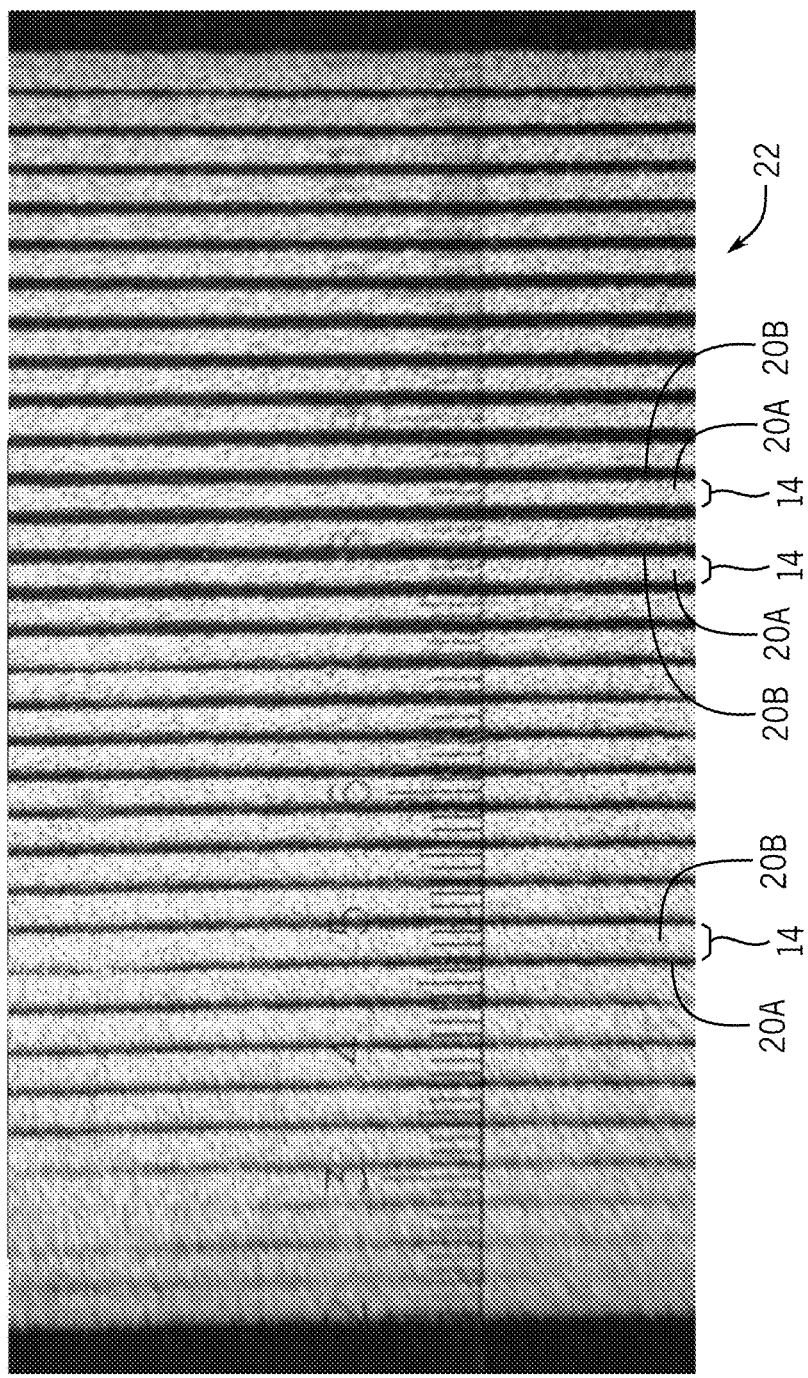
FIG. 3 is an x-ray image of an exemplary embodiment of a high contrast test pattern.

The embodiments as disclosed in the present application improve control of wafer thickness resulting in wafers produced closer to the nominal desired thickness. A closer accuracy to the nominal desired thickness results in a more accurate calibration phantom altogether. FIG. 3 depicts an exemplary embodiment of an x-ray image as exemplarily acquired in a 2D projection imaging procedure of a test pattern 22 comprised of a plurality of line pairs 14 constructed of wafers 20A, 20B having different Z values. The test pattern 22 exemplarily exhibits a 32 line pair per centimeter density. Such an exemplary embodiment of a test pattern may be produced in the manners as described in the present application.

In addition to creating inserts with high resolution test patterns capable of being used in phantoms to test the high contrast resolution of increasingly better imaging systems as will be available in the future, further exemplary embodiments of test pattern inserts may similarly be constructed. In an exemplary and non-limiting embodiment, an insert having a test pattern of a screen having a specific grid ratio may be produced and incorporated into a phantom and used for testing 2D resolution, for example in fluoroscopy or conventional radiography. In a still further exemplary embodiment, high-Z printed materials, either alone or in combination with low-Z materials may be used to produce imaging targets for use in phantoms, including, those currently provided by metal balls (e.g. bearing balls or beads), wires, or screen meshes. These test patterns may be defined in one or more test pattern design files which provide the computer readable instructions in order to operate a computer-controlled extruder in the manner as described herein to construct the test patterns. The test pattern design file may include not only dimensional definition of the test pattern, but extruder temperature, flow/extrusion rate, material selections, Z-direction increments, and/or extruder head tool paths and positions.

In the manners as described above, more complex shapes and or patterns may be produced and incorporated into phantoms, that, when imaged and processed with appropriate testing software, may be used to test slice sensitivity, slice thickness, and resolution using analysis techniques, for example, but not limited to, modulation transfer function, point spread function (ask about resolution), and noise power spectrum. Such tests may exemplarily be performed on tomography or tomosynthesis systems.

In one exemplary embodiment, a phantom constructed as shells of spherical cysts of varying CT number material. In one example, the phantom may have a core of a high-Z material in one volume surrounded by a mantle and a crust of lower Z materials. The thickness (e.g. net diameter) of each layer may be the same in embodiments, or may be of varying relative thicknesses. One example could exemplarily include an ABS+Ti core surrounded by an ABS mantle, further surrounded by a PS shell. In other exemplary embodiments, different concentrations by weight of the high-Z metal may be used to create different components of the test pattern. For example, varying concentrations by weight of $TiO_2$, $ZnO_2$, or $ZrO_2$ in ABS, PS, or PLA may be used for the different regions. It is recognized that the order and the materials may be changed or adjusted in a manner as needed, for example based upon application or use. One application example for such a phantom is to quantify volumes for diagnostic systems. Since the constructed phantom would have a known volume and diameter, a QA check can be performed against an automated detection algorithm where the detectability may vary between each material and thickness.

As described in further detail herein, in embodiments the test pattern may be constructed using at least one high-Z material and the test pattern may further be constructed of at least two materials with the same base thermoplastic material and two radiologically different characteristics. Further, the test pattern may then be embedded into another material, like a water equivalent material, for example to produce a removable phantom insert. In other embodiments, the test pattern is embedded as it is created by the further extrusion of one or more materials surrounding the test pattern.

In another exemplary embodiment, the radiographic test patterns may be constructed using techniques similar to those as used in printed electronics. In such an embodiment printing techniques are used to deposit radiographic material onto a substrate, for example, but not limited to, a substrate formed of material such as described in the above noted, U.S. Pat. No. 9,669,116, entitled, "Water-Equivalent Phantom." In one exemplary embodiment, a piezoelectric element may be used to deposit a fluid or "ink" with a high-Z value. In an exemplary embodiment, the ink may be a high-Z nanometallic silver ink.

In testing, PLA material was identified as a potentially suitable low-Z material, although other materials, including ABS as noted above may also be used. Additionally, PLA materials with various high-Z additives may be available and as noted above consistency between the base material of the low-Z and high-Z materials can help bonding between multiple materials. As presented in the table below, tests of various materials were evaluated for suitability by measuring CT Number, listed in Hounsfield Units (HU). CT data was collected at 120 kVp, 240 mAs for each sample within a 16.5 cm diameter cylindrical phantom. Images were reconstructed at 12-bit pixel depth; thus HU values range from −1024 to 3071. For the purposes of comparison, current radiological test pattern line pairs are constructed of aluminum (+2000 HU) and polystyrene (−40 HU).

TABLE 1

| Material | OEM | Corrected CT# (HU) |
|---|---|---|
| LOW Z MATERIALS | | |
| PLA White | PolyMaker - PolyMax | 106.0 |
| ABS White | Form Futura - Easy Fill | −26.5 |
| ABS Lego/Stone Gray | CoEX 3D | −26.5 |
| ASA | 3DXTech | −70.0 |
| HIGH Z MATERIALS | | |
| Iron PLA | ProtoPlant "pasta" | 2450.0 |
| Stainless Steel PLA | ProtoPlant "pasta" | 3071.0 |
| Bismuth ABS | Turner Medtech GMASS | 3071.0 |
| Copper PLA | SainSmart - China | 781.0 |
| Aluminum PLA | SainSmart - China | −64.0 |
| Titanium ABS - 25% TiO2 | IFC - Custom | 325.0 |
| Titanium ABS - 30% TiO2 | IFC - Custom | 455.0 |
| Zinc ABS - 5% ZnO | IFC - Custom | 85.0 |
| Zinc ABS - 10% ZnO | IFC - Custom | 235.0 |

As can be seen in the table above, the FePLA material produced a suitable high-Z value without saturating the CT reconstruction system. Similarly, PLA material provided a suitable low-Z value compared to the legacy Aluminum-Polystyrene system.

Still other materials may be used in addition to the ones as noted above. Acrylonitrile-styrene-acrylonitrile (ASA) polymers may also be used as the base material in addition to ABS, PLA, or PS materials as described above. These base polymers may exhibit a low-Z characteristic as noted in the table above. High-Z filler may be added to the base polymers to increase the CT number of the resulting material. These filler materials may include but are not limited to: $Al_2O_3$, Al powder, $TiO_2$, CuO, CuS, ZnO, ZnS, $ZnSO_4$, Zn Stearate, and Iron Oxide(s). Filler materials may also include zinc oxide, titanium dioxide, and zirconium dioxide. In an exemplary embodiment, ABS+$TiO_2$ material may be used. This material may be in concentrations of $TiO_2$ at 25% or 30% by weight. The particular use application and the base polymer may specify the % weight ranges for the added filler material. Exemplary and non-limiting weight ranges may be between 5% to 70% although this depends upon the high-Z material, the Z value of the material itself and the base material. Some high-Z materials may be suitable in concentrations of 10-30% w/w, while other materials may be suitable at 60-70% w/w. In general, heavier materials may provide a suitable HU value for the resulting material while using less material overall, and in some cases lower weight percentages.

In exemplary embodiments, the high-Z material is at least 350 HU contrast from the low-Z material. In other embodiments the HU contrast may be 2000 HU, 2500 HU, or greater. However, as noted above, in some embodiments, too great of HU contrast, particularly from too high of HU values can saturate CT reconstructions while influencing and biasing neighboring pixels. Therefore in embodiments, the high-Z material is below 3000 HU at 120 kVp. In embodiments, the high-Z filler is selected relative to the base polymer to balance the resulting high-Z material to yield the desired effective atomic number (Zeff) and electron density such that a radio transmission of diagnostic x-rays into the high-Z material is similar to that of Aluminum.

The materials used in exemplary embodiments have presented challenges in constructing embodiments of the test patterns as disclosed herein. In evaluating suitable high-Z materials, considerations for both the manufacturability of the material to be used in the computer-aided manufacturing techniques described above, including, but not limited to printing, FFF, and FDM techniques, as well as the resulting CT number of the test pattern constructed with the high-Z material. In a still further consideration, the resulting CT numbers of the test patterns must be within the operable resolution of CT reconstruction systems. Currently most CT reconstruction systems are 12-bit systems which saturate at +3071HU. Some newer systems are 16-bit systems which have a higher saturation limit, but for current purposes, this consideration must be made. Therefore, by way of reference to Table 1 above, high-Z materials with HU values greater than or equal to 3071 (e.g. ABS+Bi) saturate 12-bit systems and impair the CT reconstructions intended to be tested and calibrated. In still further embodiments, high-Z materials that would otherwise saturate CT reconstruction systems, may still be suitable for use in 2D test patterns or for test patterns for testing 2D imaging systems, where 3D reconstruction, and the resulting saturation, is not needed. Further, in exemplary embodiments, the Z value doping metals when combined with the base material polymer, make the resulting material too viscous or otherwise resistant to flow or have a plastic transition phase that lends itself to clogging the material extrusion heads at the resolution required in embodiments of the test patterns disclosed herein. This has exemplarily been found to be the case with embodiments using PLA/Iron PLA materials.

Figure 4:
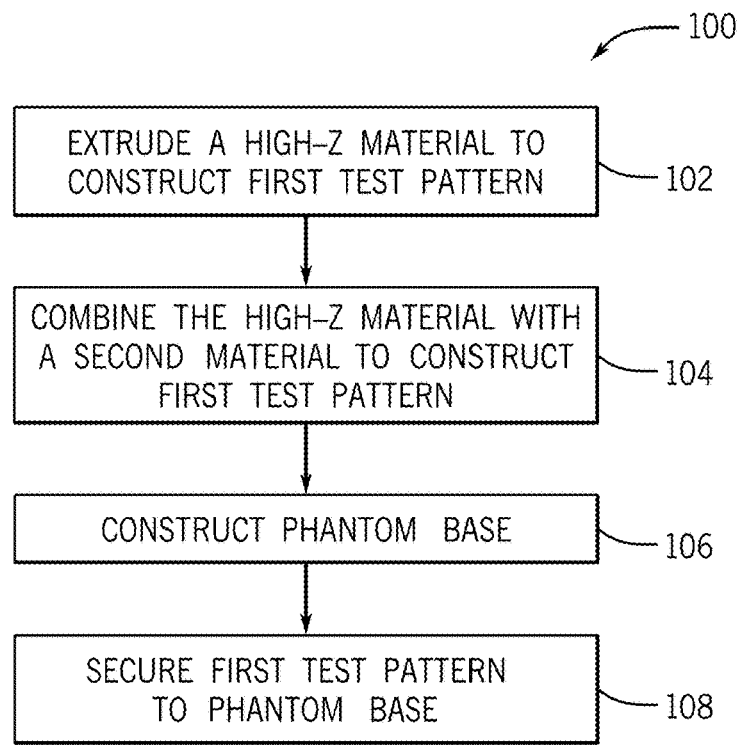
FIG. 4 is a flow chart that depicts an exemplary embodiment of a method of constructing a radiological calibration device.

FIG. 4 is a flow chart that depicts an exemplary embodiment of a method 100 of constructing a radiological calibration device. The method 100 begins at 102 where a high-Z material is extruded to construct a first test pattern. In exemplary embodiments, the extrusion of the high-Z material can be filament extrusion, a sheet extrusion or a deposition of the high-Z material. In exemplary embodiments, the high-Z material also has a relatively low melting point or glass transition phase, for example as provided by a thermoplastic material. In exemplary embodiments, a thermoplastic based material includes a high-Z metal additive to manipulate one or more radiological characteristics of the base material.

At 104, the high-Z material is combined with a second material to construct the first test pattern. In exemplary embodiments, the first test pattern includes a plurality of features, a plurality of features each comprising different materials of the high-Z material and the second material. In exemplary embodiments, the test patterns are line pairs of alternative high-Z and low-Z materials. In such an embodiment, the second material may be a low-Z material. In a still further exemplary embodiment, the second material is the base material such that the second material and the high-Z material comprise the same base material, but are radiologically distinct due to the high-Z metal additive to the high-Z material.

It will further be recognized that the combination of the high-Z material with the second material may be performed in a number of ways. In a first embodiment, the combination may be sheet extrusions of the high-Z material and the second material such as to form sequential layers of the high-Z material and the low-Z material. In another embodiment, the first test pattern may be constructed of the high-Z material and the first test pattern embedded within the second material, for example by injection molding or casting of the second material about the first test pattern constructed of the high-Z material. In a still further exemplary embodiment, both of the high-Z material and the second material are extruded from a numerically controlled extrusion head. In this embodiment, the numerically controlled extrusion head may be operable to simultaneously and/or sequentially extrude the high-Z material and the second material to construct the first test pattern.

At 106, a phantom body is constructed. The phantom body may be constructed of a radiologically neutral material, in an exemplary embodiment such radiologically neutral material may be a water equivalent material. In other embodiments, the phantom body may be constructed of the second material, the base material, or a further combination of the base material and an additive material such that the phantom material is radiologically distinct from the high-Z material and the second material. The phantom body may be constructed separately from the first test pattern. In an alternative embodiment, the phantom body is further constructed using the numerically controlled extrusion head, and the phantom body is constructed in a manner sequential to and/or simultaneous with the extrusion of the high-Z material and extrusion of the second material to construct the first test pattern.

At 108, the first test pattern is secured to the phantom body. In the exemplary embodiments as disclosed herein, the first test pattern may be constructed separately from the construction of the phantom body and the first test pattern may therefore be removably secured to the phantom body. In another exemplary embodiment, the first test pattern and the phantom body and constructed by operation of the numerically controlled extrusion head such that the first test pattern and the phantom body are secured to one another by intra-material diffusion between the high-Z material, the second material, and the material of the phantom body.

It will be recognized that in exemplary embodiments, the radiological calibration device that includes the first test pattern and the phantom body may further include a plurality of operative region, each operative region including a test pattern. In an exemplary and non-limiting embodiment, the calibration device includes a plurality of operative regions arranged within the phantom body and each operative region includes a test pattern constructed in the manners as described above and in which the test patterns each include a plurality of line pairs. The test patterns of each of the operative regions include line pairs of varying line pair thicknesses between the test pattern. Each test pattern of the calibration device comprises a distinctive thickness between the line pairs of the test pattern.

In exemplary embodiments, at least one of the test patterns includes line pairs less than 200 microns thick.

Figure 5:
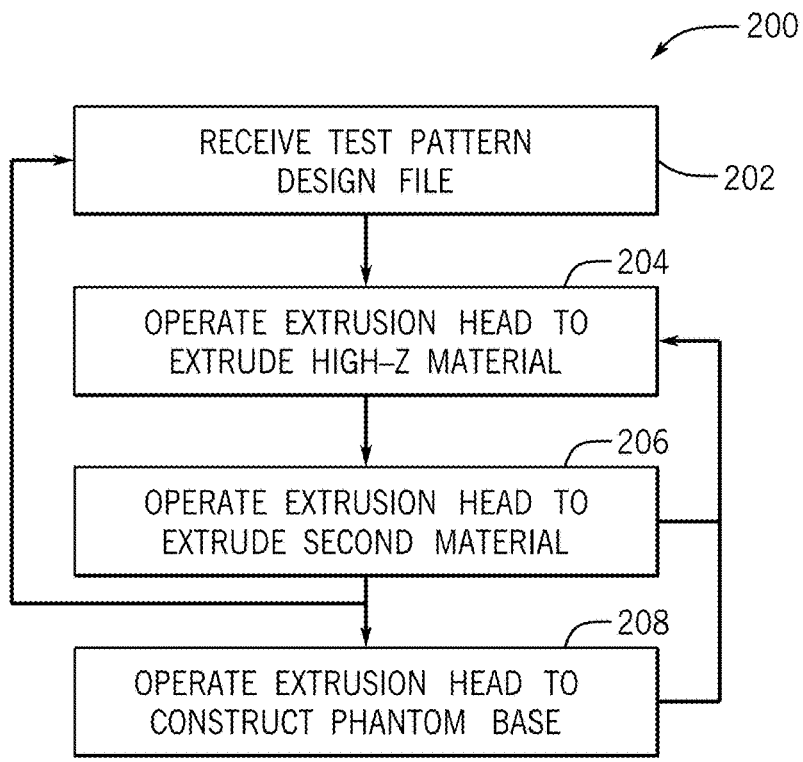
FIG. 5 is a flow chart that depicts an exemplary embodiment of a method of constructing a radiological calibration device.

FIG. 5 is a flow chart that depicts an exemplary embodiment of a method 200 of constructing a radiological calibration device. It will be recognized that there may be overlap between embodiments carrying out the method 100 and the method 200 and that neither is mutually exclusive of the other.

At 202, a test pattern design file is received. In exemplary embodiments, the test pattern design file may be received in a variety of ways. In one exemplary embodiment, the test pattern design file may be constructed from at least one medical image of a patient, subject, or sample. In still further exemplary embodiments, the test patterns may be data files that include computer readable instructions and that include at least some of a dimensional definitions of the test pattern, extrusion head temperatures, material flow or extrusion rate, material selection, Z-direction increments, extrusion layer thicknesses, and/or extrusion head tool pens and positions. The test pattern design file may be stored on a non-transient computer readable medium in a manner accessible by a controller associated with a numerically controlled extrusion head. The controller may exemplarily be a processor or microprocessor that communicatively connected to the aforementioned non-transient computer readable medium upon which the test pattern design file is stored, as well as being communicatively connected to further non-transient computer readable media upon which computer executable code is stored such that the controller, upon execution of code, acquires the test pattern design file and upwrites to provide control command to the numerically controlled extrusion head according to the first test pattern design file in order to carry out the extrusions and operations as described herein to construct the test pattern as well as the radiological calibration device.

At 204, the numerically controlled extrusion head is operated by the commands provided by the controller according to the test pattern design file to extrude a high-Z material according to the test pattern design file exemplary embodiments, the high-Z material exemplarily exhibits a CT number between 2,000-3,000 at 100 KVP while having a low melting point or glass transition phase such that it is extrudable through the extrusion head and exhibits sufficiently low viscosity at extrusion head temperatures such as to meet the resolution of the test pattern design files.

Either sequential to or simultaneous to the operation of the extrusion head to extrude the high-Z material, the numerically controlled extrusion head is operated at 206 to extrude a second material. It will be recognized that in exemplary embodiments, such extrusion heads may provide the ability to operate with multiple different materials at the same time either to extrude simultaneously or in rapid sequence. Therefore, in an exemplary embodiment, the test pattern design file includes instructions for use of differing materials in different portions of the test pattern. In an exemplary embodiment, the second material comprises a same base of material as the high-Z material and the high-Z material differs from the second material due to a white by weight percentage of a high-Z metal additive to the base material. In exemplary embodiments, the base material is a low-Z material and is exemplarily a thermoplastic material which provides the thermal and viscosity properties as described above.

The simultaneous and/or sequential extrusion of the high-Z material and the second material, both of which include the same base thermoplastic material, facilitates the securing of components of the test pattern, for example layers or wafers in a line pair by inter-material diffusion due to both the high-Z material and the second material being above their glass transition phases when sequentially or simultaneously extruded.

In exemplary embodiments, the controller may operate the numerically controlled extrusion head according to the test pattern design file between extrusion of the high-Z material and the second material to complete the first test pattern. It will be recognized that in still further exemplary embodiments, test patterns may include still further materials. In such embodiments, each of the materials extruded to form the test pattern may comprise the same thermoplastic base material while each of the extruded material are radiologically distinct from one another in at least one radiological property. It will be recognized that additional test pattern design files may be accessed and received by the controller and the numerically controlled extrusion head operated to create a plurality of test patterns within a single radiological calibration device.

At 208, the numerically controlled extrusion head is further operated by the controller to construct a phantom body surrounding the one or more test patterns constructed by the extrusion head in the radiological calibration device. In exemplary embodiments, one or more of the test pattern design files may further include the numerically controlled extrusion head instructions to construct the phantom body, or the phantom body may have its own design file stored at the non-transient computer readable medium and accessible by the controller such that the numerically controlled extrusion head may be operated accordingly. In exemplary embodiments, the extrusion head may be operated to sequentially extrude the material of the phantom body during extrusion of the high-Z material and the second material to construct the at least one test pattern. In such an embodiment, the one or more test patterns may be constructed by extrusion simultaneous to the construction of the phantom body also by extrusion about the test patterns. It will be recognized that in exemplary embodiments, the phantom body is constructed of a material that comprises the same base material as the high-Z material and the second material as described above, such that the phantom body and the test pattern may be secured together by inter-material diffusion. In exemplary embodiments, the phantom body is constructed of a radiologically neutral material. In an exemplary embodiment, such radiologically neutral material may be radiologically distinct from the high-Z material and from the second material. In a still further exemplary embodiment, the radiologically neutral material may be a water-equivalent material.

Citations to a number of references are made herein. The cited references are incorporated by reference herein in their entireties. In the event that there is an inconsistency between a definition of a term in the specification as compared to a definition of the term in a cited reference, the term should be interpreted based on the definition in the specification.

In the above description, certain terms have been used for brevity, clarity, and understanding. No unnecessary limitations are to be inferred therefrom beyond the requirement of the prior art because such terms are used for descriptive purposes and are intended to be broadly construed. The different systems and method steps described herein may be used alone or in combination with other systems and methods. It is to be expected that various equivalents, alternatives and modifications are possible within the scope of the appended claims.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of constructing a radiological evaluation device, the method comprising:
   constructing a first test pattern by extruding a first material according to a first test pattern design file, the first material being a high Z material;
   constructing the first test pattern by combining the first material with a second material, the first material being radiologically distinct from the second material;
   constructing a phantom body; and
   securing the first test pattern to the phantom body.

2. The method of claim 1, wherein the phantom body is constructed of a radiologically neutral material, and the radiologically neutral material is a water equivalent material.

3. The method of claim 1, wherein constructing the first test pattern comprises simultaneously extruding the first material and the second material, wherein the extrusion of the second material is according to the first test pattern design file.

4. The method of claim 1, wherein constructing the first test pattern comprises sequential extruding the first material, then extruding the second material, wherein the extrusion of the second material is according to the first test pattern design file.

5. The method of claim 1, further comprising:
   constructing the first test pattern by extruding the second material according to the first test pattern design file;
   stopping extrusion of the first material; and
   continuing construction of the first test pattern by extruding a third material according to the first test pattern design file, the third material being radiologically distinct from the first material and the second material.

6. The method of claim 5, wherein a first portion of the first test pattern comprises the first material and the second material, and a second portion of the first test pattern comprises the second material and the third material.

7. The method of claim 1, wherein the first test pattern is constructed simultaneous to construction of a portion of the phantom body and both the first test pattern and the phantom body are constructed by 3D printing.

8. The method of claim 1, wherein a first portion of the first test pattern is constructed by extrusion of the first material, and the second material forms a second portion of the first test pattern surrounding the first portion.

9. The method of claim 1, further comprising:
operating a 3-D printer according to the first test pattern design file to extrude the first material and to extrude the second material to construct the first test pattern.

10. The method of claim 1, wherein the first test pattern comprises alternating layers of the first material and the second material, wherein the second material is a low-Z material and the first material comprises the low-Z material in combination with a metal additive to form the high-Z material.

11. The method of claim 10, wherein the metal additive is zinc oxide.

12. The method of claim 1, further comprising:
constructing a plurality of test patterns, wherein the plurality of test patterns comprises the first test pattern; and
wherein each test pattern of the plurality of test patterns comprises alternating layers of the first material and the second material, wherein the second material is a low-Z material and the first material comprises the low-Z material in combination with a metal additive, and each test pattern of the plurality of test patterns comprises a different thickness of the alternating layers of the first material and the second material.

13. The method of claim 1, further comprising:
constructing the first test pattern by extruding the second material according to the first test pattern design file; and
constructing the first test pattern by extruding a third material according to the first test pattern design file;
wherein the first material, second material, and third material are each different from the other two in at least one of physical density, electron density, CT number, or attenuation.

14. The method of claim 1, wherein the radiological evaluation device comprises:
a first operative region comprising at least the first material and the second material, the first operative region comprising:
the first test pattern comprising the first material and the second material secured to the first material.

15. The method of claim 14, wherein the first operative region further comprises a third material surrounding the first test pattern.

16. The method of claim 14, wherein the first test pattern comprises alternating layers of the first material and the second material forming a series of line pairs across the first test pattern.

17. The method of claim 16, wherein each layer of the alternating layers is less than 200 microns in thickness.

18. The method of claim 16, wherein the second material is a base material and the first material is the base material in combination with a metal additive to create the high-Z material.

19. The method of claim 18, wherein the base material has a CT number between −200 and 200 at 120 kVp.

20. The method of claim 18, wherein the base material is ABS plastic.

21. The method of claim 20, wherein the metal additive is zinc-oxide.

22. The method of claim 16, wherein each layer of the alternating layers is a 3-dimensional layer having a thickness less than 200 microns, a height, and a depth.

23. The method of claim 22, wherein the depth of each layer of the alternating layers extends through the operative region.

24. The method of claim 14, wherein the phantom body comprises a radiologically neutral material, wherein the first operative region is secured within the phantom body.

25. The method of claim 24, wherein the phantom body comprises an aperture and the first operative region is a phantom insert configured to be removably secured within the aperture.

26. The method of claim 1, wherein the high-Z material has a CT number greater than 300 and less than 3000 HU at 120 kVp.

27. The method of claim 1, wherein the radiological evaluation device comprises:
a first operative region comprising the test pattern comprising the first material and the second material secured to the first material, wherein the first material comprises a first thermoplastic base material and the second material comprises a second thermoplastic base material.

* * * * *